United States Patent [19]
Wallach

[11] 3,930,505
[45] Jan. 6, 1976

[54] SURGICAL APPARATUS FOR REMOVAL OF TISSUE

[75] Inventor: Mark Wallach, New York, N.Y.

[73] Assignee: Hydro Pulse Corporation, New York, N.Y.

[22] Filed: Dec. 2, 1974

[21] Appl. No.: 528,810

Related U.S. Application Data

[63] Continuation-in-part of Ser. No. 481,952, June 24, 1974, abandoned, which is a continuation-in-part of Ser. No. 285,002, Aug. 30, 1972, Pat. No. 3,818,913.

[52] U.S. Cl. .................................. 128/305; 128/276
[51] Int. Cl.² .................... A61B 17/32; A61M 1/00
[58] Field of Search ............ 128/276, 278, 297, 305

[56] References Cited
UNITED STATES PATENTS

| | | |
|---|---|---|
| 3,589,363 | 6/1971 | Banko et al.............................. 128/276 |
| 3,812,855 | 5/1974 | Banko................................. 128/276 |
| 3,818,913 | 6/1974 | Wallach............................... 128/305 |

*Primary Examiner*—Channing L. Pace
*Attorney, Agent, or Firm*—Howard C. Miskin

[57] ABSTRACT

Defective or unwanted tissue is removed such as from the lens of an eye by directing a pulsating high velocity liquid jet onto the defecting tissue to disintegrate the tissue and sucking the liquid entraining the disintegrated tissue from the area adjacent the tissue by a suction conduit. A control system is provided to insure the proper amount of suction. The control system also monitors the suction conduit and in response to a sudden change in pressure resulting from a clogging condition, the sucking action is reversed causing pressure to be forced through the conduit. Salt crystals can be added into the liquid stream of the pulsating liquid to improve the cutting action.

24 Claims, 13 Drawing Figures

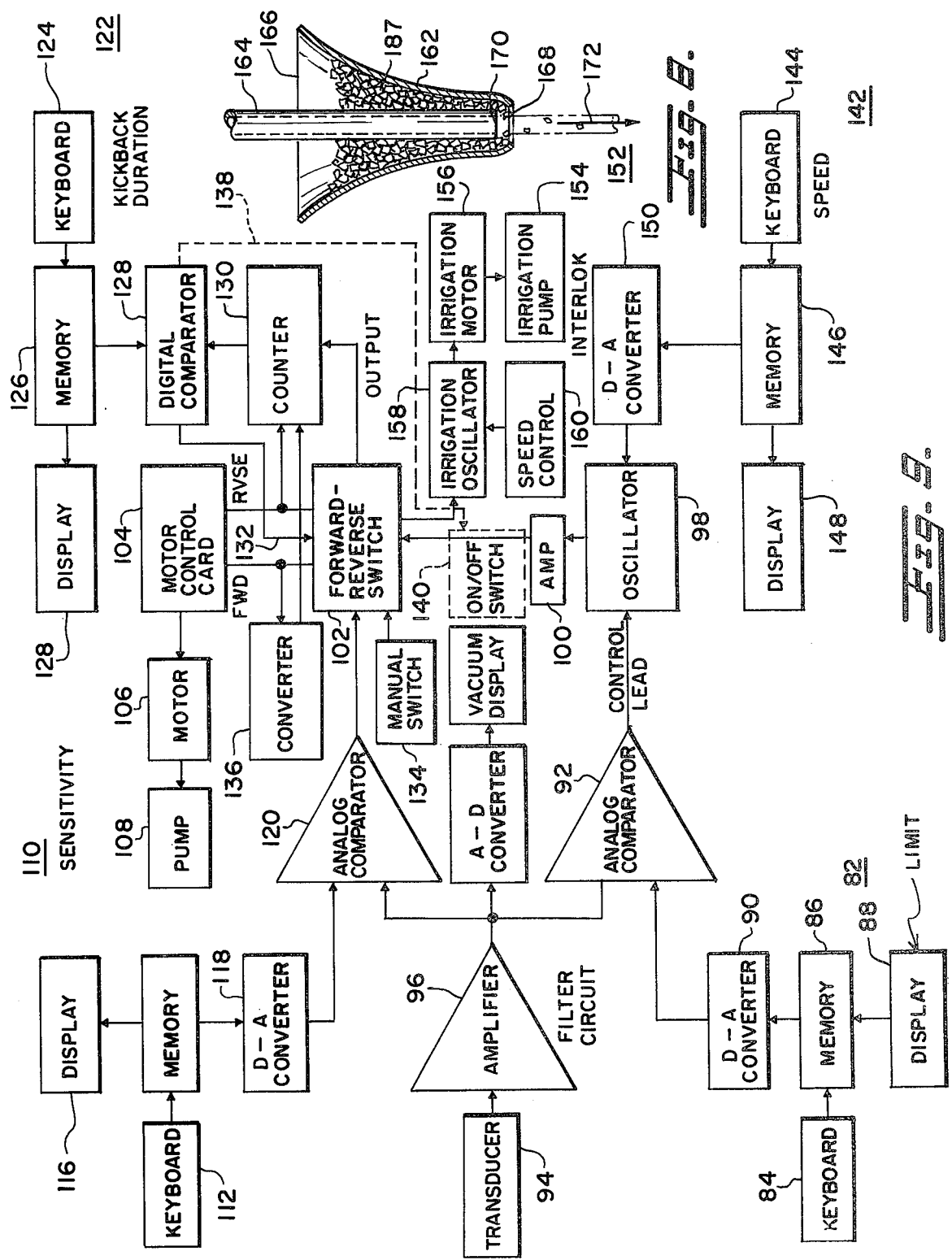

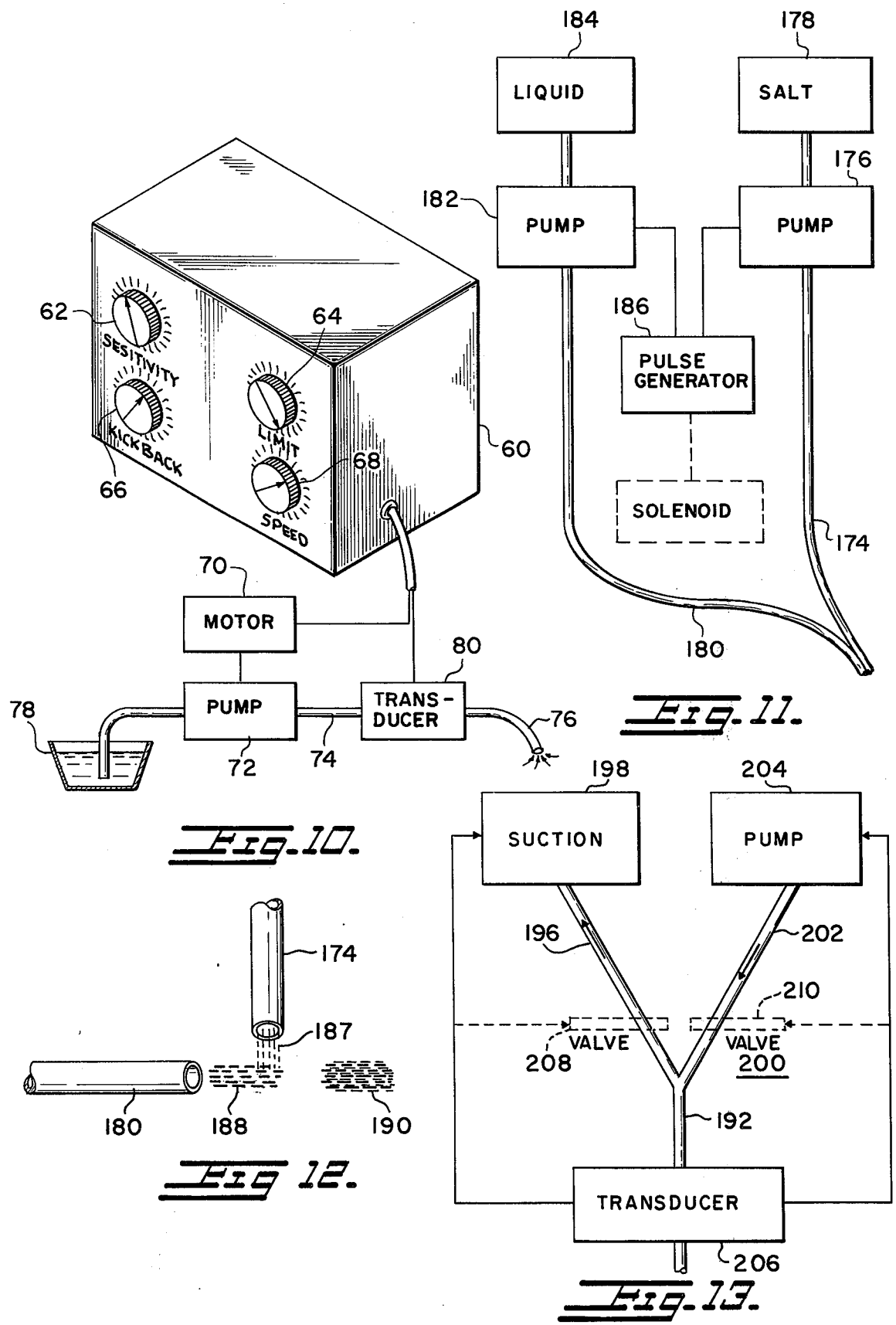

SURGICAL APPARATUS FOR REMOVAL OF TISSUE

BACKGROUND OF THE INVENTION

This application is a continuation-in-part of application Ser. No. 481,952 filed on June 24, 1974 and now abandoned, which in turn was a continuation-in-part of application Ser. No. 285,002 filed Aug. 30, 1972 now U.S. Pat. No. 3,818,913.

The present invention relates generally to improvements in surgical procedures and apparatus and it relates more particularly to an improved method and apparatus for the disintegration and removal of selected sections of animal tissue.

These are numerous surgical procedures which require the removal of selected protions of tissue of an extremely delicate nature with a minimum or no interference with or damage to the surrounding or otherwise healthy tissue. Such procedures are frequently required in surgical operations connected with the eye, such as in the removal of cateracts and similar surgical procedures. The methods and equipment heretofore employed and proposed are awkward and highly time consuming in their use, require an extremely high degree of skill, are often accompanied by damage to adjoining healthy tissue and frequent failure and otherwise leave much to be desired.

Instruments having a vibrating element such as a chisel, or emitting pulses have been used for cutting of material for some time for various uses. For example, a vibrating element using a slurry for cutting has been used for dental work and industrial applications with limited success in limited work areas. As is apparent, when used in inaccessible areas, a small inadvertent movement of the chisel can damage tissue adjoining the tissue desired to be removed.

SUMMARY OF THE INVENTION

It is a principal object of the present invention to provide an improved surgical method and apparatus.

Another object of the present invention is to provide an improved method and apparatus for disintegrating or fragmenting animal tissue in a preselected area and removing such disintegrated tissue from said area.

Still another object of the present invention is to provide an improved method and apparatus for disintegrating and removing animal tissue from a predetermined area without adversely affecting the surrounding tissue and which prevents excessive suction build-up.

A further object of the present invention is to provide an improved method and apparatus for disintegrating and removing tissue from inaccessible areas with a minimum of adverse effect of the surrounding and masking tissue.

Still a further object of the present invention is to provide a method and apparatus of the above nature characterized by their reliability, simplicity, fine areas of operation, great versatility and adaptability and case of application even in delicate and highly hazardous environments.

Yet another object of the present invention is to provide a control system for regulating the proper amount of suction within the suction conduit and automatically turning off the source of suction when the amount of suction exceeds predetermined limits.

Still another object of the present invention is to provide an automatic detection control system which detects a change in pressure in the suction conduit resulting from a clogging condition and automatically causes a reversal of the directional flow of fluid within the conduit.

A further object of the present invention is to provide a control system which regulates the speed of operation of the suction source to control the flow in the suction conduit.

Yet another object of the present invention is to provide a method and apparatus for introducing salt crystals into the liquid stream ejected from the nozzle.

The above and other objects of the present invention will become apparent from a reading of the following description taken in conjunction with the accompanying drawings which illustrate preferred forms of the improved apparatus.

In a sense the present invention is predicated on the discovery that hardened animal tissue in a closely confined and restricted area can be disintegrated or finely fragmented by directing a fine pulsating high velocity jet onto the desired area and sucking the liquid of the impinging jet which has entrained or emulsified therein the disintegrated tissue. The area of treatment can be very precisely delineated and obviates the need for any alteration, severance and significant penetration of any adjacent or overlying tissue. Also, the incision can be kept very small as contracted to standard surgical techniques. The jet is produced by a very fine nozzle and the tissue entraining liquid is likewise withdrawn by a very fine conduit. Advantageously, any clogging of the suction conduit by the tissue is eliminated by reversing the liquid flow in the suction conduit in response to a sharp pressure drop therein. Excessive suction build-up can damage an organ of the body, such as an eyeball by collapsing the cornea. Also, the jet quickly dissipates its energy when it impinges onto a yielding surface. This is critical especially when the present suction is used in connection with eye surgery such as removing a hardened lens of the eye, with the tissue surrounding the lens being resilient.

The liquid jet may contain no abrasive material and is advantageously an isotonic solution of slight alkalinity, for example, of a pH of about 7.4, but could be any liquid containing desired additives, such as anti-infection/coagulants. The pulse frequency of the jet is advantageously widely variable, depending on the specific organ with which it is used, and can vary from one pulse every few seconds, up to 333 pulses per second (20,000 ppm.). Further, for some applications a continuous fine steam of liquid can be used. The pressure is variable between about 15 and about 3500 pounds per square inch, preferably between 125 to 1800 p.s.i., and its velocity at the point of impingement between about 50 and about 500 feet per second. The liquid jet diameter at the point of impingement is advantageously of a diameter between about 0.001 and about 0.010 of an inch and may be formed of a single jet stream or a plurality of converging jet streams. The volume of the discharge pulse is 20.0 lambda to 0.25 lambda.

The inlet port to the suction conduit may be annular and surround the liquid jet or it may be at the center of converging jets or adjacent to a jet either parallel or perpendicular to the jet.

The improved method and apparatus may be employed in very delicate and confined areas of little accessibility with a minimum of secondary surgery, and separates organs and tissues without damage, and is very versatile, adaptable and easy and convenient to operate with a minimum of side effects and hazards.

A control aparatus permits the presetting of a limit on the amount of suction, and also measures the pressure in the suction conduit such that when the suction pressure gets below the preset limit the suction pump will automatically shut off. The control system also includes a presettable sensitivity limit such that when the pressure in the suction conduit gets above the sensitivity limit, indicating a clog in the conduit, the suction pump will stop operating and instead liquid will automatically be supplied at above atmospheric pressure to the suction line thereby removing the clogged condition. A speed control is also included, whereby the speed of operation of a motor driving the suction pump can be preset. An irrigation tube which is used to provide a constant flow of irrigation fluid to the tissue, is interconnected to the control system such that when the suction pump is reversed to provide a positive pressure, the irrigation flow will temporarily stop. A duration system is included which can be used in conjunction with the suction pump to select the volume of evacuation required. Additionally, the duration system can be used to determine the duration of the positive pressure applied to release a clogged condition in the suction conduit.

An additional auxiliary conduit can be used in conjunction with a source of crystal salt which can be added into the pulsating liquid stream to provide a saline solution which aids in increasing the cutting speed of the apparatus. The auxiliary conduit supplying the salt crystals can be interconnected with the pulse generator controlling the pulsating liquid so that a corresponding packet of salt crystals will be provided for each pulse of liquid.

BRIEF DESCRIPTION OF THE DRAWINGS

FIG. 8 is an enlarged sectional view illustrating the addition of the salt crystals to the apparatus;

FIG. 9 is a schematic block diagram of the control system for controlling the suction operation;

FIG. 10 is a perspective view of the control system including the features of the present invention;

FIG. 11 is a schematic block diagram of an auxiliary conduit for supplying the salt crystals;

FIG. 12 is an enlarged view of the ends of the tubes shown in FIG. 11; and

FIG. 13 is a schematic block diagram of a Y-configuration of the suction conduit in accordance with another embodiment of this invention.

DESCRIPTION OF THE PREFERRED EMBODIMENTS

Figure 1:
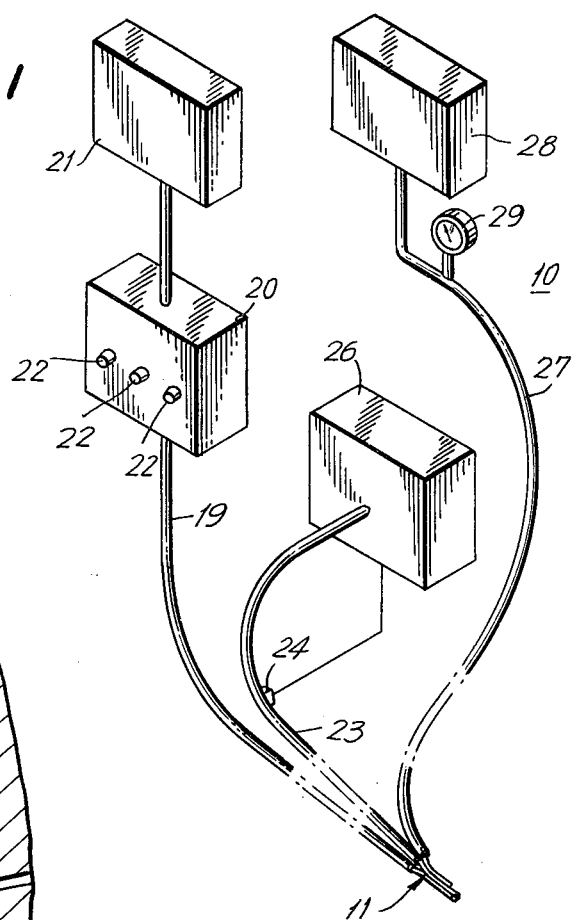
FIG. 1 is a perspective view of an apparatus embodying the present invention.
Figure 2:
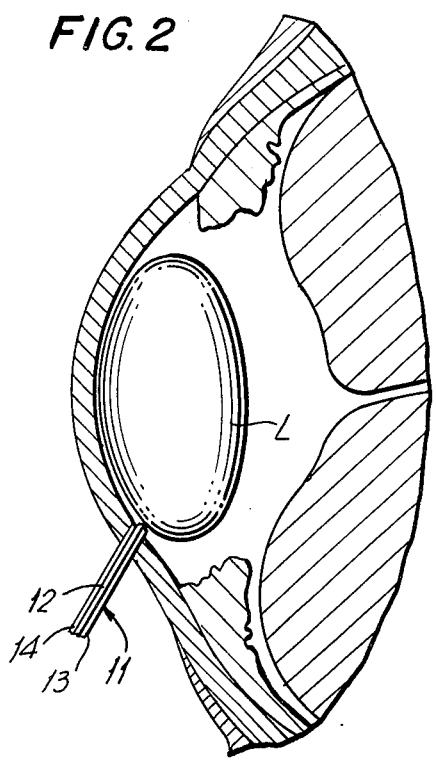
FIG. 2 is a fragmentary sectional view illustrating the application of the apparatus of FIG. 1 to the treatment of eye lens tissue.
Figure 3:
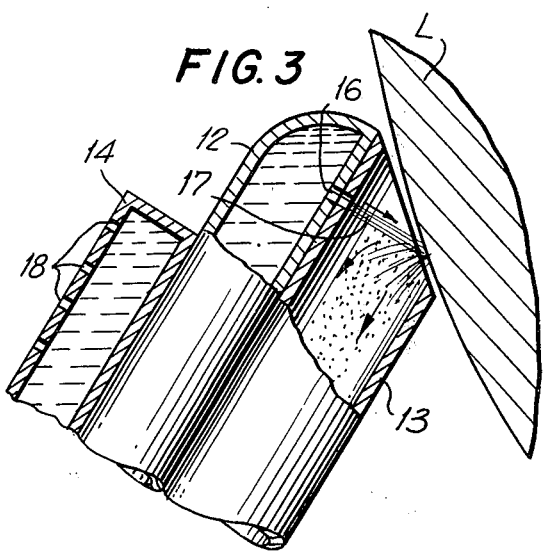
FIG. 3 is an enlarged fragmentary view partially in section of one form of nozzle and suction tip of the apparatus of FIG. 1.

Referring now to the drawings, and particularly FIGS. 1 and 3 thereof which illustrate a preferred embodiment of the present invention, the reference numeral 10 generally designates the improved apparatus which is employed to great advantage in practicing the present improved process in the removal of unwanted tissue from the lens of a human eye, such as a cataract or the like. The apparatus comprises a fine hand implement 11 which is manipulated by the surgeon and includes three fine tubes joined along their lengths as an integral unit, a nozzle tube 12, a suction tube 13 and a drainage or bathing tube 14. The maximum transverse dimension of the assembled tubes advantageously does not exceed one hundred fifty thousandths of an inch (0.150 inch), each tube having an inside diameter of between about ten and sixty-five thousandths of an inch (0.0101 to 0.065 inch and an outside diameter of between about twenty and seventy-seven thousandths of an inch (0.020 to 0.077), the length of the working tip of the assembly advantageously being about three-quarters of an inch (3/4 inch) for optical applications. Tube length can vary for other surgical applications.

The distal end of tube 12 is curved and closed and it is arranged side by side with suction tube 13 whose distal end is open and shortly rearwardly of the distal end of tube 12. A nozzle defining circular port 16 is formed in the joined adjacent walls of tubes 12 and 13 and is directed parallel to the suction or inlet port 17 of suction tube 13. The drainage liquid tube 14 extends somewhat less than the full lengths of tubes 12 and 13 and is provided along its distal length with small outlet ports 18. It should be noted that the diameter of the nozzle port 16 is advantageously between 0.001 and 0.010 of an inch.

The proximate end of the nozzle tube 12 is connected by a high pressure highly flexible tube 19 to the outlet of an adjustable pulsing liquid feed device 20 whose inlet is connected to an elevated tank 21 containing an isotonic solution of the composition previously described. The pulsing device 20 may be of any conventional construction in which the pulse frequency, pulse duration, pressure and liquid volume velocity output are continuously adjustable by knobs or by corresponding foot operated controls. For example, the device 20 may include a positively displacement pressure pump, such as a piston pump whose stroke is adjustable and which is driven by a variable speed electric motor and is provided with an adjustable pressure relief or bypass valve so that the above variable and adjustable parameters are easily and conveniently achievable. Of course other systems serving the same functions may be employed.

The proximate end of the suction tube 13 is connected by a flexible tube 23 to a vacuum or suction pump 26 to withdraw any liquid and entrained tissue from the area of the suction port 17. Advantageously, a vacuum of between 76 and 304 mm. of mercury has been found satisfactory for eye surgery applications for the suction. However, it can vary according to the surgical application. A pressure sensing element 24 communicates with the tube 23 and is so adjusted that when the suction in tube 23 rises above or conversely when the pressure falls below a predetermined level consequent to the clogging of tube 13 or 23 by tissue sucked up by the tube, it reverses the suction pump 26 to reverse the flow in tubes 13 and 23 a predetermined amount to eject the clogging tissue. Following the ejection of the clogging material the suction pump 36 returns to its normal functioning. The reverse flow in pipe 13 and 23 may be for successive predetermined intervals until they are unclogged as evidenced by the proper pressure sensed by element 24.

The irrigating pipe 14 is connected by a flexible tube 27 to an elevated tank 28 by way of a valve 29 the tank 28 containing any suitable washing solution, for example of the composition of the liquid contained in tank 21. This irrigating fluid helps maintain the pressure in the eye and prevents the cornea from collapsing. It should be noted that the flexible tubes 19, 23 and 27 are joined side by side as a highly flexible assembly thereby greatly facilitating the convenient handling and manipulation of the instrument 11.

In employing the apparatus 10 in operating on the eye, for example in the removal of a cataract, the usual precautions are observed and a small incision i.e., about one hundred seventy-five thousandths of an inch (0.175 inch) is made in the masking tissue, for example in the sclera, to provide access for entry of the instrument 11 into optimum engagement with the unwanted tissue. The lens L to be treated may be in its normal position, but advantageously is prolapsed into the anterior chamber.

The instrument 11 is inserted through the performed incision into confronting engagement with the unwanted tissue and the pulser 20, and vacuum unit 26 is actuated and the valve 29 is opened, the various parameters being adjusted to optimum conditions as dictated by experience and an specified above.

A pulsating high velocity fine liquid jet is directed through the nozzle port 16 onto the area of unwanted tissue of lens L to fragment, disintegrate and emulsify the jet-subject tissue, and the jet liquid containing the entrained and emulsified tissue is sucked up by suction unit 26. The liquid from the tube 14 keeps the eye bathed in the desired manner. The instrument 11 is then manipulated until all the unwanted tissue is fragmented and removed and the instrument 11 is then retracted and the usual post operative procedures followed. It should be noted that in the event that a large tissue fragment is detached and lodges in tube 13 to clog the tube 13 the action of the vacuum unit 26 is reversed in response to the pressure sensing device 24 to eject the clogging tissue, which is further fragmented by the jet so that it may be properly withdrawn by the suction tube 13. Also, since the tissue surrounding the lens is soft and yielding, the jet energy is absorbed by the wall if the jet stream happens to miss the target tissue.

Figure 4:
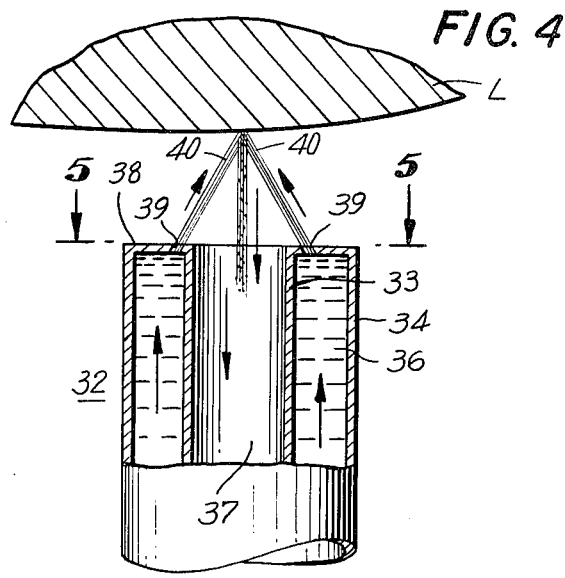
FIG. 4 is a view similar to FIG. 3 of another tip structure.
Figure 5:
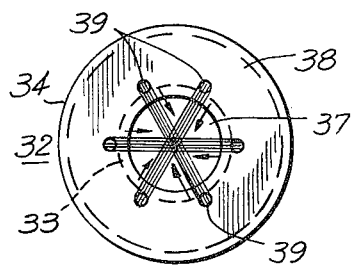
FIG. 5 is a sectional view taken along line 5—5 in FIG. 4.

The apparatus illustrated in FIGS. 4 and 5 differs from the apparatus 10 primarily in the construction of the instrument 32 which corresponds to the instrument 11. Specifically the instrument 32 includes a pair of coaxial inner and outer tubes 33 and 34 respectively which delineate an annular outer conduit 36 and an inner axial conduit 37. The distal end of outer conduit 36 is closed by an annular end wall 38 provided with circumferentially spaced nozzle defining ports 39 which are directed toward a common central point coaxial with the conduits 36 and 37 and forwardly thereof.

The outer conduit 36 is connected by a flexible tube to a liquid pulsing device corresponding to the pulsing device 20 and the central conduit 37 is connected to a suction pump corresponding to vacuum unit 26, likewise by a flexible hose.

The operation of the apparatus employing the instrument 32 is similar to that using the instrument 10. A plurality of pulsating high velocity jets 40 from nozzle 39 converge on a point located on the unwanted tissue in lens L to disintegrate the jet subjected tissue which is entrained in the jet liquid and sucked into and withdrawn through the central suction tube 37.

Figure 6:
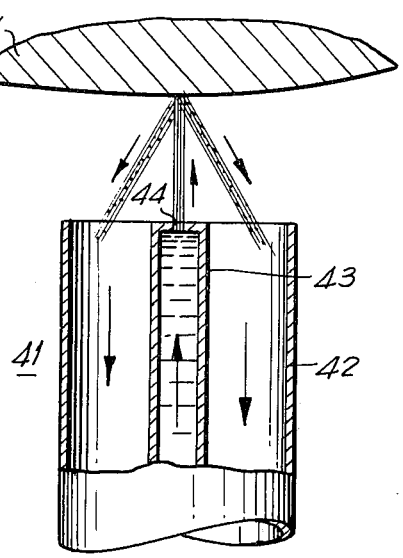
FIG. 6 is a view similar to FIG. 3 of still another form of tip.

The instrument 41 illustrated in FIG. 6 differs from that last described primarily in that the pulsating jet emanates from the axial tube and the tissue entraining liquid withdrawn by the surrounding outer annular tube. The instrument 41 includes an outer suction tube 42 open at its distal end and connected by a flexible hose to a suction device corresponding to device 26 and a coaxial tube 43 closed at its distal end and provided with a nozzle defining port 44. The tube 43 is connected by a flexible hose to a liquid pulsing device corresponding to device 20 and the apparatus is employed in the manner earlier described.

Figure 7:
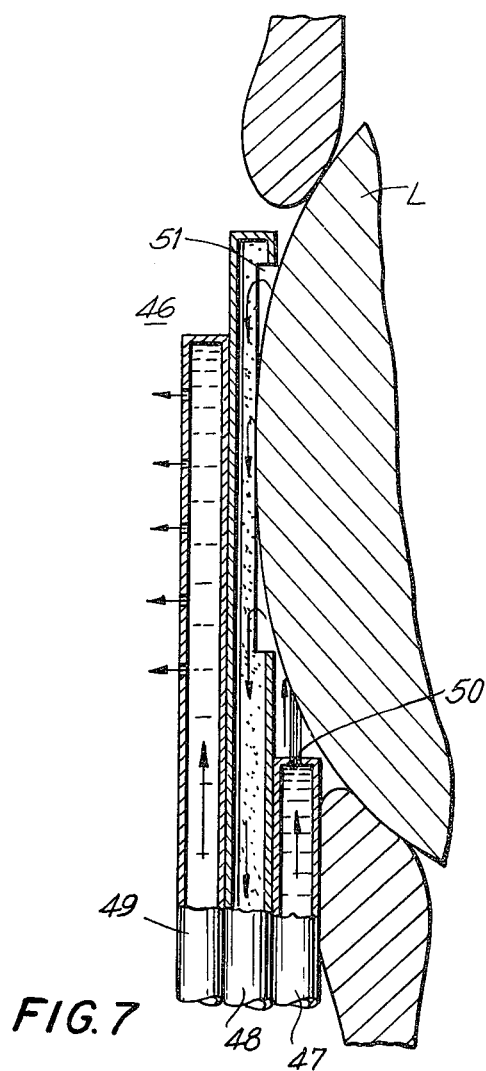
FIG. 7 is a view similar to FIG. 3 showing a further tip structure.

In FIG. 7 of the drawings there is shown another form of tissue removing instrument differing from those first described primarily in that the pulsating liquid jet is directed at an angle to the tissue approaching tangency and the liquid section port extends beyond the nozzle for an extended distance. Specifically the improved instruments 46 include three interconnected rigid side by side longitudinal tubes 47, 48 and 49 respectively. The tube 47 is closed at its distal end and has a nozzle defining centrally located port 50 formed in the front thereof and is connected by a flexible tube to a pulsating liquid source corresponding to the device 20. The second tube 48 is disposed alongside the tube 47 and projects beyond the front end of tube 47 and is closed at its front end. An elongated suction opening 51 is formed in the side wall of tube 48 on the side of tube 47 and extends from a point forward of the distal end of tube 47 to substantially the distal end of tube 48. The tube 49 is a bathing liquid tube and is secured to the outer face of tube 48 and is provided with a plurality of longitudinally spaced outlet ports. The tubes 48 and 49 are connected by corresponding flexible tubes to a vacuum unit corresponding to unit 26 and to a bathing liquid tank corresponding to tank 28 respectively.

The instrument is employed in the manner similar to those earlier described except that the pulsating jet emerging from the nozzle 50 is at an obtuse angle to the treated tissue and directs the tissue entraining liquid toward the large suction opening 51.

Referring now to FIG. 10, there is shown a perspective view of the control system for the suction conduit. The control system includes an instrument box 60 which has four presetable dials, namely a sensitivity dial 62, a limit dial 64, a kickback duration dial 66, and a speed dial 68. Electrically coupled to the instrument box is a motor 70 which drives a suction pump 72. Fluid is drawn by the suction pump 72 into the suction conduit 74 at its distal end 76 and discharged into a collection vessel 78. A transducer 80, such as a pressure sensing device, is interconnected to the control box 60 and provides an electrical output indicating the pressure in the suction conduit.

FIG. 9 shows a schematic block diagram of the control system and would be included in the instrument box of FIG. 10. The control system has a limit section, shown generally at 82, which includes an input device, such as keyboard 84. The input device could also be a dial or other similar device, which can be preset in accordance with a desired value. The value preset is stored in a memory 86, and simutaneously displayed on display 88, such as a meter or an alphanumeric display. If the value preset is in a digital format, the value is converted to an analog value by a digital to analog converter 90. The output analog value then serves as one input to analog comparator 92. A transducer 94, which could include the pressure sensing device connected to the suction conduit, provides an output which is first amplified and filtered by circuit 96, and then serves as the other input to analog comparator 92. When the transducer voltage exceeds the preselected limit set on the keyboard 84, analog comparator 92 provides an output control signal which acts upon the control lead of oscillator 98. The output of oscillator 98 is amplified by amplifier 100, and then passes through the forward-reverse switch 102, and the motor control card 104, to drive motor 106 which in turn operates suction pump 108. Thus, the output from analog comparator 92 acts to stop oscillator 98, and thereby stop the operation of the suction pump 108. The limit section 82, therefore serves to provide an upper limit for the amount of suction in the suction conduit and prevents an excessive amount of suction from the tissue area being removed. This provides a safety feature which prevent damage to the tissue or nerves which might otherwise be accidently aspirated as a result of an excessive amount of suction. The keyboard can be calibrated in inches of mercury to represents the actual value of suction desired.

Frequently, the suction conduit gets clogged as a result of a large piece of tissue getting stuck in the conduit, whereby a drop in pressure suddenly occurs. The control system can automatically detect such sudden drops in pressure, and in response terminate the suction. Also, it can then provide a positive pressure flow through the suction conduit in a opposite direction, to thereby remove the clog. The control system which carries out this operation is included in the sensitivity section 110, which contains a keyboard 112, on which there can be preset a limit of pressure. The keyboard, or other type of input device, can be calibrated in inches of mercury. The value preset is stored in memory 114 and simultaneously displayed on display 116. If a digital input is utilized, the digital signal is converted by the digital to analog converter 118, whose output is applied as one input to the analog comparator 120. The other input to comparator 120 comes from the amplified and filtered output of transducer 94. The actual amount of suction in the suction conduit will thereby be compared to the preset sensitivity limit. When the actual transducer level exceeds the preset sensitivity level analog comparator 120 produces an output which acts upon the forward reverse switch 102 to change from a forward state to a reverse state. The reverse output from switch 102 is applied to the motor control card 104 which reverses the operation of motor 106 so that the pump 108 will provide a positive atmospheric pressure to the suction conduit rather than a suction pressure.

The length of time during which pump 108 will operate in a reverse state can also be preset using the kickback duration section 122. This section includes keyboard 124, wherein there can be preset the duration of time during which the pump operates in reverse. The keyboard could alternately be any other type of input device as has heretofore been described. The duration time which is preset, is stored in memory 126 and at the same time displayed on display device 128. The value stored in memory 126 is applied as one input to a digital comparator 128. A counter 130 is connected to the reverse input to the motor control card 104, whereby the counter receives the pulses from the oscillator during reverse operation of the motor. The number of pulses during the reverse operation is counted and compared with the preset time in the comparator 128. When the comparator detects an equality, it signals the forward reverse switch 102 along line 132, which changes the state of the switch back to its forward direction, whereby the oscillator pulses will now drive the motor and the pump in a forward direction so that the pump again serves as an evacuation pump for the suction conduit.

The combination of the sensitivity section 110 and the kickback duration section 122 together operate to automatically respond to any clogging condition and can operate in an exceedingly fast response time. Additionally, a manual switch 134 can be connected to the forward-reverse switch, whereby the motor can manually be reversed thereby changing the operation of the pump from an evacuation pump to a pressure pump. This manual switch 134 can be utilized at the discretion of the operator to provide a forward pressure through suction conduit.

To enable the operator to choose a preselective volume of evacuation, it is possible to preset the control system for a giving duration of pulse, whereby only a predetermined amount of volume would be evacuated. To accomplish this, the kickback duration section 122 is utilized for the forward operation of the motor which drives the pump as an evacuation pump. A converter circuit 136 is included, and can typically be a simple switch that interconnects the counter 130 to the forward line of the motor control cord 104 to receive the forward pulses from the oscillator to the motor. The number of forward pulses can initially be preset on keyboard 124 and the preset number would then be compared in digital comparator 130 with the actual number of forward pulses coming from the oscillator. When the digital comparator recognizes an equality, a signal is sent on line 138 to a main on-off switch 140 which is included along the electric line interconnecting the oscillator 98 with the motor 106.

The keyboard 124 can be calibrated directly in volume, wherein the number of pulses represent a prefixed amount of volume of evacuation. The on-off switch 140 could be a simple control gate which disconnects the oscillator from the motor when the predetermined amount of evacuation volume is reached.

The speed of operation of the oscillator producing the pulses which drive the motor and pump, can also be preset in the speed section 142. Keyboard 144 is utilized to preset the amount of speed. This value is stored in memory 146 and at the same time displayed on display device 148. If a digital input is utilized, the value is converter by digital to analog converted 150 to an analog value which serves as the input to the oscillator 98.

As has heretofore been explained, in addition to the main tube which provides the pulsating liquid, and the suction tube which removes the liquid, there can also be included a drainage tube which provides an irrigation fluid to keep the tissue in a constant bath of irrigating liquid. When the suction tube is being operated in reverse, whereby a positive pressure is sent through the suction conduit, it would be preferable to halt the flow of the irrigating fluid to prevent build up of excessive fluid volume around the tissue being removed. The control system can therefore also include an interlock section 152 which interconnects the operation of the forward-reverse switch 102 with a pump 154 sending the irrigation fluid through the irrigation conduit. The irrigation pump 154 would be driven by a motor 156 controlled by an oscillator 158. The oscillator 158 can be directly interconnected with the forward-reverse switch 102, whereby as the forward-reverse switch is changed to a reverse state, a control signal is sent to the irrigation oscillator 158 to stop its oscillations, which thereby stops the irrigation pump 154 to temporarily halt the flow of the irrigation fluid. When the forward-reverse switch is set back to its forward state, the control signal is removed, and the irrigation oscillator again commences operation to drive the irrigation fluid through the drainage tube. A speed control 160 can also be included with the irrigation oscillator 158. This speed control 160 can resemble the speed section 152, heretofore described.

Each of the various switches which have been previously identified could either be hand switches or alternately foot switches which could simplify their manipulation during the course of a surgical procedure. Thus, the manual switch 134, as well as the switch of the convertor 136 could be foot control switches, or any other type of well known switch.

Also, it has been found to increase the cutting speed and scope of apparatus 10 shown in FIG. 1, grains of salt can be introduced into the liquid jet stream leaving nozzle tube 12. The salt crystals aid in the cutting action and readily dissolve in the jet liquid in the body cavity to form a saline solution. The rate of dissolving of the salt crystals is slow enough so that they perform their cutting action before they are fully dissolved. The salt crystals may be added by various means, including suction resulting from the jet stream flow through the nozzle, by a vibrating feed, not shown or other controlled feed means.

Referring now to FIG. 8 there is shown one embodiment for providing the crystal salt, including a conical shaped container 162 which is coaxial with the main liquid flow tube 164. The conical container includes an input end 166 which permits the insertion of the crystal salt. The output end 168 of the conical container is spaced from the output end 170 of the flow tube 164 along an axial direction of flow shown as along line 172. As the pulsing liquid flows out of tube 164, it will draw with it some crystal salt from the container 162 to form a saline solution. The conical shape of the container provides an additional benefit in permitting a constant flow of the crystal salt toward its output end without the possibility of collecting in a mass along the way. Furthermore, the reduced section at the neck of the conical container permits a control of the volume of crystal salt to be drawn into the pulsing liquid.

Referring to FIG. 11 there is shown another apparatus for introducing the crystal salt, wherein a separate auxiliary conduit 174 is utilized. A pump 176 is located at the inlet end of the auxiliary conduit 174 and pumps salt crystals from a source of salt 178 into the conduit 174. The main liquid flow conduit 180 also includes a pump 182 and a source of liquid 184, as heretofore explained. A pulse generator 186, which could typically be an oscillator, is coupled to drive the pump 182 providing the flow of the pulsating liquid. The pulse generator 186 is also interconnected to the pump 176 providing the crystal salt, whereby a unit of crystal salt will be pumped in conjunction with each pulse of liquid.

Referring now to FIG. 12 there is shown an enlarged view of the output ends of the auxiliary conduit 174 and the main conduit 180, having the output axes of the two conduits perpendicular to each other whereby the unit of crystal salt 187 perpendicularly enters into the pulse of liquid 188 to form pulses of a saline solution 190.

While a suction pump was disclosed which was reversed in response to a sensing element to unplug the suction tube, two pumps can be used connected by a "Y" joint. The suction pump can be stopped when the suction line or nozzle becomes plugged and a separate pump immediately begins operation forcing fluid out through the suction line to unplug the suction tube or port and then the sequence is reversed to continue the suction. This two-motor step reduces the return of tissue and other debris.

Referring now to FIG. 13 the Y joint is shown, and includes the suction tube 192 having a suction conduit 196 which includes the suction pump 198 at the end. Connected at a Y joint shown generally at 200, is an auxiliary conduit 202 having a pump 204 coupled at the end thereof. A transducer 206, which could include a pressure sensing device, is placed along the tube 192 to sense the reversal of pressure resulting from a clogged condition. When such a change in pressure is sensed, the transducer sends a signal to stop the suction pump 198, and instead to start the pressure pump 204. Optionally, valves 208 and 210 could be placed within the respective conduits 196 and 202 so that when the suction pump 198 is stopped, the valve 208 will be closed, and alternatively, when the pump 204 is stopped, the valve 210 will be closed. The valves will therefore prevent the flow of liquid through the wrong conduit.

The suction level of the suction tube as used herein can be controlled by the control system described above that it can be used as a manipulator to lift or hold organs during an operation or experiment. The suction can be so controlled that it converts the suction tube into a delicate holding tool, which can release the organ by a slight amount of pressure through the tube. Similarly, the suction can be preprogrammed to remove a preselected volume in small increments. For example, 40 lambda of fluid from the inner ear can be removed in four steps of 10 lambda each.

While separate liquid sources are shown, a single source may be used. Also, instead of a pump to produce the pressure for the jet, the source of liquid can be pressurized, such as by a pressurized tank, and a pulser only used. Also, while the jet stream from the tip is shown generally cylindrical, it may expand slightly to a conical shape; however, the area of contact should be kept as small as possible. Further, while the jet openings in the various embodiments above were illustrated as circular, other shapes can be used.

While there have been described and illustrated preferring embodiments of the present invention, it is apparent that numerous alterations, omissions and additions may be made without departing from the spirit thereof.

What is claimed is:
1. An apparatus for disintegrating and removing animal tissue from a preselected enclosed area comprising a hand manipulatable first tube having a distally dis- posed outlet port, a liquid pulsating pump having an inlet and an outlet, a source of liquid connected to said pump inlet, means including a flexible conduit connecting said first tube to said pump outlet, a suction conduit including an outlet port disposed proximate said first tube outlet port, a source of suction, and means including a flexible conduit connecting said suction conduit to said source of suction, said pump providing a stream of pulsating liquid through said first tube outlet port at a frequency between ¼ to 333 pulses per second, at a pressure about atmospheric pressure of about 15 to about 3,500 p.s.i. and having a velocity of between 50 and 500 feet per second.

2. The apparatus of claim 1 including control means for supplying liquid at above atmospheric pressure to the suction line in response to the suction source being removed from the suction line.

3. The apparatus of claim 2 and wherein said control means includes sensitivity input means for selecting a predetermined level of suction, transducer means providing an output responsive to the pressure in said suction conduit, level comparison means for comparing the transducer output with said predetermined level of suction and producing a control signal when said transducer output falls below said predetermined level, and motor control means coupled to said source of suction and responsive to said control signal for stopping said source of suction and introducting a pressure flow into said suction conduit.

4. The apparatus of claim 3 wherein said motor control means includes motor means for driving said source of suction, and a reversing switch means coupled between said motor means and said level comparison means for reversing the operation of said motor means in response to said control signal, whereby said source of suction provides a pressure flow into said suction conduit.

5. The apparatus of claim 4 and wherein said control means further includes duration input means for selecting a predetermined interval during which said motor means is operated, counter means controlled by said reversing switch means and coupled to said motor means for counting the interval during which said motor means operates in reverse, and interval comparison means for producing a duration output signal when the interval counted by said counter means reaches said predetermined interval, said duration output signal being coupled to said reversing switch means for returning said motor means to forward operation.

6. The apparatus of claim 4 and including manual switch means coupled to said reversing switch means for manually reversing the operation of said motor means.

7. The apparatus of claim 4 including an irrigation tube having at least one outlet port disposed proximate said first tube outlet port, a source of drainage fluid and interconnecting means including a flexible conduit connecting said irrigating tube to said source of drainage fluid.

8. The apparatus of claim 7 and wherein said irrigation tube extends somewhat less than the full length of said first tube.

9. The apparatus of claim 7 and wherein said interconnecting means includes an irrigation pump means for pumping said drainage fluid from said source of drainage fluid through said drainage tube, and wherein said control means includes interlocking means interconnecting said irrigation pump means with said reversing switch means whereby when said reversing switch means respond to said control signal said irrigating pump means is stopped.

10. The apparatus as in claim 2 and wherein said control means includes limit input means for selecting a limit level of suction, transducer means providing an output responsive to the pressure in said suction conduit, limit level comparison means for comparing the transducer output with said predetermined limit level and producing a control signal when said transducer output gets above said limit level and motor control means coupled to said source of suction and responsive to said control signal for stopping said source of suction.

11. The apparatus of claim 1 and wherein said source of suction includes an evacuation pump, a motor controlling said evacuation pump, an oscillator supplying said motor, and speed control means coupled to said oscillator and capable of being preset in accordance with a desired speed of motor operation.

12. The apparatus of claim 5 including evacuation control means coupled between said counter means and said motor means permitting said counter to count the interval during which said motor means operates in a forward direction, said predetermined interval preset on said duration input means representing a forward interval, and further including turn-off switch means interconnecting said interval comparison means with said motor means for turning off said motor means when said forward interval counted equals said predetermined interval.

13. The apparatus of claim 1 and including auxiliary means for introducing salt crystals into the pulsating liquid flowing out of the first tube outlet port.

14. The apparatus of claim 13 and wherein said auxiliary means includes a container having an input end for inserting therein salt crystals, and an output port, said container being in a coaxial position with respect to said first tube, the output port of said container being spaced from the output port of said first tube in the direction of flow of the pulsating liquid, whereby as liquid is pumped from said first tube outlet port, salt crystals will be drawn into said liquid.

15. The apparatus of claim 14 and wherein the shape of said container is conical with its narrow end being adjacent the output port thereof.

16. The apparatus of claim 13 and wherein said auxiliary means includes an auxiliary tube having an outlet port disposed proximate said first tube outlet port, the axis of said auxiliary tube lying in a plane generally perpendicular to the axis of said first tube outlet port, said auxiliary means further including a source of crystal salt, and interconnecting means including a flexible conduit conecting said auxiliary tube to said source crystal of salt.

17. The apparatus of claim 16 and wherein said interconnecting means further includes valve means coupled to said flexible conduit to regulate the passage of salt therethrough, said valve means being electrical interconnected with said liquid pulsating pump, whereby a unit of salt is emitted from said auxiliary tube corresponding to each pulse of liquid flowing from said first tube.

18. The apparatus of claim 2 and including a second pump, an auxiliary flexible conduit connected to said second pump, joining means forming a Y joint which interconnects said suction conduit with its respective flexible conduit and with said auxiliary flexible conduit, and wherein said control means includes means responsive to a change in pressure in said suction conduit for stopping operation of said source of suction and commencing operation of said second pump.

19. The apparatus of claim 18 and wherein said control means includes valve means for blocking the auxiliary flexible conduit when said source of suction is operating and blocking the flexible conduit connected to said source of suction when said second pump is operating.

20. The method of disintegrating and removing animal tissue from a preselected enclosed area with a nozzle having a working tip comprising the steps of:
   a. generating a stream of liquid pulses leaving the nozzle having a frequency of about ¼ to about 333 pulses per second;
   b. adjusting the rate of velocity of said stream of liquid from about 50 to about 500 feet per second;
   c. simultaneously directing the pulsating liquid jet onto a confined area of said tissue to disintegrate said tissue into small particles to form a suspension of particles in said liquid and sucking the suspension of particles of said tissue from said preselected area at a suction of between 76 and 304 mm. of mercury.

21. The method of claim 20 including the step of removing said suction and introducing a pressure flow of liquid responsive to the clogging of the flow of said sucked liquid.

22. The method of claim 20 including the step of introducing salt crystals into the stream of liquid pulses.

23. The method of claim 22 and wherein said step of introducing salt crystals includes the step of providing a unit of salt crystals for each pulse of liquid.

24. The method of claim 21 and wherein said step of removing said suction includes the step of reversing the operation of a suction pump to provide a positive pressure flow.

* * * * *